(12) United States Patent
Dunphy et al.

(10) Patent No.: US 10,881,313 B2
(45) Date of Patent: *****Jan. 5, 2021

(54) EMERGENCY CARDIAC AND ELECTROCARDIOGRAM ELECTRODE PLACEMENT SYSTEM

(71) Applicant: CB Innovations, LLC, Escondido, CA (US)

(72) Inventors: Stephen Dunphy, Carlsbad, CA (US); Christian McClung, Rancho Santa Fe, CA (US); Sean Ronan, Carlsbad, CA (US)

(73) Assignee: CB Innovations, LLC, Escondido, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 15/990,651

(22) Filed: May 27, 2018

(65) Prior Publication Data

US 2018/0271394 A1 Sep. 27, 2018

Related U.S. Application Data

(63) Continuation of application No. 15/853,578, filed on Dec. 22, 2017, now Pat. No. 9,986,929.

(60) Provisional application No. 62/465,752, filed on Mar. 1, 2017.

(51) Int. Cl.
*A61B 5/0408* (2006.01)
*A61B 5/00* (2006.01)
*A61B 5/0428* (2006.01)

(52) U.S. Cl.
CPC ...... *A61B 5/04085* (2013.01); *A61B 5/04087* (2013.01); *A61B 5/04286* (2013.01); *A61B 5/6841* (2013.01); *A61B 2505/01* (2013.01); *A61B 2562/0209* (2013.01); *A61B 2562/046* (2013.01); *A61B 2562/222* (2013.01); *A61B 2562/227* (2013.01)

(58) Field of Classification Search
CPC .................. A61B 5/04085; A61B 5/04286
See application file for complete search history.

(56) References Cited

U.S. PATENT DOCUMENTS

| | | | | |
|---|---|---|---|---|
| 4,082,086 A * | 4/1978 | Page | ................ | A61B 5/04085 600/391 |
| 6,847,836 B1 * | 1/2005 | Sujdak | ............... | A61B 5/04085 600/382 |
| 8,019,402 B1 * | 9/2011 | Kryzpow | ........... | A61B 5/04085 600/386 |
| 9,320,446 B2 * | 4/2016 | Gillberg | ............. | A61B 5/04085 |
| D800,321 S * | 10/2017 | Roche | .......................... | D24/187 |

(Continued)

OTHER PUBLICATIONS

International Search Report for PCT/US2018/019682 field on Feb. 26, 2018.

*Primary Examiner* — Lee S Cohen
(74) *Attorney, Agent, or Firm* — Clause Eight IPS; Michael Catania

(57) ABSTRACT

An emergency cardiac and electrocardiogram (ECG) electrode placement device is disclosed herein. The emergency cardiac and electrocardiogram (ECG) electrode placement device incorporates electrical conducting materials and elastic material into a pad that is applied to a chest wall of a patient, which places multiple electrodes in the appropriate anatomic locations on the patient to quickly obtain an ECG in a pre-hospital setting.

5 Claims, 17 Drawing Sheets

(56) References Cited

U.S. PATENT DOCUMENTS

| | | | |
|---|---|---|---|
| 9,986,929 B1* | 6/2018 | Dunphy | ............ A61B 5/04085 |
| 2009/0253975 A1 | 10/2009 | Tiegs et al. | |
| 2012/0323104 A1 | 12/2012 | Readinger et al. | |
| 2014/0373785 A1 | 12/2014 | Burnes et al. | |

* cited by examiner

EMERGENCY CARDIAC AND ELECTROCARDIOGRAM ELECTRODE PLACEMENT SYSTEM

CROSS REFERENCES TO RELATED APPLICATIONS

The Present Application is a continuation application of U.S. patent application Ser. No. 15/853,578, filed on Dec. 22, 2017, now U.S. Pat. No. 9,986,929, issued on Jun. 5, 2018, which claims priority to U.S. Provisional Patent Application No. 62/465,752, filed on Mar. 1, 2017, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to ECG devices.

Description of the Related Art

The electrocardiogram (ECG) is an essential test that provides medical professionals with essential information in the management of patients with a variety of conditions. It is not only of significant importance in the evaluation and management of patients with chest pain, but also in patients with shortness of breath, syncope, dizziness, seizures, altered mental status, stroke, psychiatric conditions, overdose, palpitations and many other conditions. It is a bulky system with a multitude of wires and connections.

The ECG provides critical data to the health care provider in managing patients with multiple medical issues. The time to obtain this data is critical and often delayed by the current technology. Minutes can become critical in the patient with an acute myocardial infarction (heart attack).

Historically, there is training in the interpretation of ECG data, as well as placement of electrodes on the chest of each patient in anatomically specific positions.

Current ECG placement is done by technicians and providers of varying medical background, including paramedics, health care technicians, nursing assistants, nurses, and doctors. The current technology is bulky, with many wires and cables. The placement of the electrodes in the acquisition of an ECG is specific and requires special training. ECG acquisition is often limited and/or delayed by multiple factors such as body sweat, ability to transport the ECG device into confined areas, performance of concomitant medical procedures such as cardiopulmonary resuscitation (CPR). Because of many limitations, medical providers must make rapid decisions and potentially delay medical care while ECG testing is done. As emergency medicine providers, the inventors have identified a need for more rapid placement of the ECG electrodes, a more portable and manageable system that will not compromise medical care, and the need to eliminate electrode placement errors.

Sujdak, U.S. Pat. No. 6,847,836 for an Emergency ECG Electrode Chest Pad discloses a chest adapted for use in an emergency room.

Dominguez, U.S. Pat. No. 6,560,473 for a Disposable ECG Chest Electrode Template With Built-In Defibrillation Electrodes discloses a template that carries ten electrodes.

Most of the prior art involves developing non-conforming devices that have to be sized independently and are impractical in the confined quarters of an ambulance. Most of the prior art does not address the ability to withstand the application to a chest wall that is diaphoretic or rapidly moving. The devices are bulky and often have a large footprint thereby obviating the application of other support devices or obscuring radiologic studies. There is very little attention to the ability to reduce the frequency of lead detachment. Nor is there much attention to conforming to multiple ECG recording devices which typically occurs during periods of transfer of care from pre-hospital to emergency department to inpatient units. The need to obtain serial measurements with a high degree of reproducibility is also missed by the prior art as subtle physiologic changes can suggest significant pathology warranting immediate intervention.

BRIEF SUMMARY OF THE INVENTION

The present invention is an emergency cardiac and electrocardiogram (ECG) electrode placement device ("EXG device") that incorporates electrical conducting materials and elastic material into a pad that is applied to the chest wall placing the electrodes in the appropriate anatomic locations on a patient. The EXG device solves the problem of lead detachment, lead reversal, inability to apply leads due to extremes in physiology, and lack of reproducibility to measure subtle changes. The ease of use with EXG device allows for acquisition of ECGs that would not have been obtained and therefore limits the opportunity loss of delays in diagnosis and treatment.

Creation of this device will reduce the time to complete an electrocardiogram (ECG) in the pre-hospital and emergency setting, eliminate systematic error in placement and interpretation of an ECG electrode, maintain and place electrodes in the proper anatomic locations across all body types, will not delay management in critical case, maintain proper skin contact through different physiologic responses such as sweat, cold and heat, as well as through medical treatment such as CPR, be easy to train providers in application and placement of ECG electrodes, and be adaptable to scenarios where space and situations limit ECG placement.

One aspect of the present invention is an emergency cardiac and electrocardiogram (ECG) electrode placement device. The device comprises a body, electrodes, cables and an electrode connector. The body preferably comprises a first extension member, a second extension member, a third extension member, a fourth extension member and a fifth extensions member. The body preferably comprises a base layer composed of a flexible material, an adhesive layer composed of a flexible material, and a backing layer attached to an adhesive surface of the adhesive layer. Each of the electrodes comprises a connection stud, a contact pad interface and a contact pad. The electrode connector is positioned on the body. Each of the second extension member, the third extension member, the fourth extension member and the fifth extension member extends outward from the first extension member. Each cable of the plurality of cables is positioned between the base layer and the adhesive layer, and connected to a corresponding electrode of the plurality of electrodes and connected to the electrode connector. The first extension member comprises a first electrode, a second electrode, a third electrode, a fourth electrode, a fifth electrode and a sixth electrode of the plurality of electrodes. A seventh electrode of the plurality of electrodes is positioned at a far end of the second extension member. An eight electrode of the plurality of electrodes is positioned at a far end of the third extension member. A ninth electrode of the plurality of electrodes is positioned at a far end of the fourth extension member. A tenth electrode of the plurality of electrodes is positioned at a far end of the fifth extension member.

Another aspect of the present invention is an emergency cardiac and electrocardiogram electrode placement device comprising a cable management module, a body, a plurality of electrodes and a plurality of cables. The cable management module comprises an upper cover, an upper guide piece, a lower guide piece and a lower cover wherein each of the upper guide piece and the lower guide piece has a plurality of channel therein. The body is composed of a first extension member, a second extension member, a third extension member, a fourth extension member and a fifth extensions member. The body comprises a base layer composed of a flexible material, an adhesive layer composed of a flexible material, and a backing layer attached to an adhesive surface of the adhesive layer. Each of the plurality of electrodes comprises a connection stud, a contact pad interface and a contact pad. Each of the second extension member, the third extension member, the fourth extension member and the fifth extension member extends outward from the cable management module. Each cable of the plurality of cables is positioned between the base layer and the adhesive layer, routed through a channel of the plurality of channels, and connected to a corresponding electrode of the plurality of electrodes and the electrode connector.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
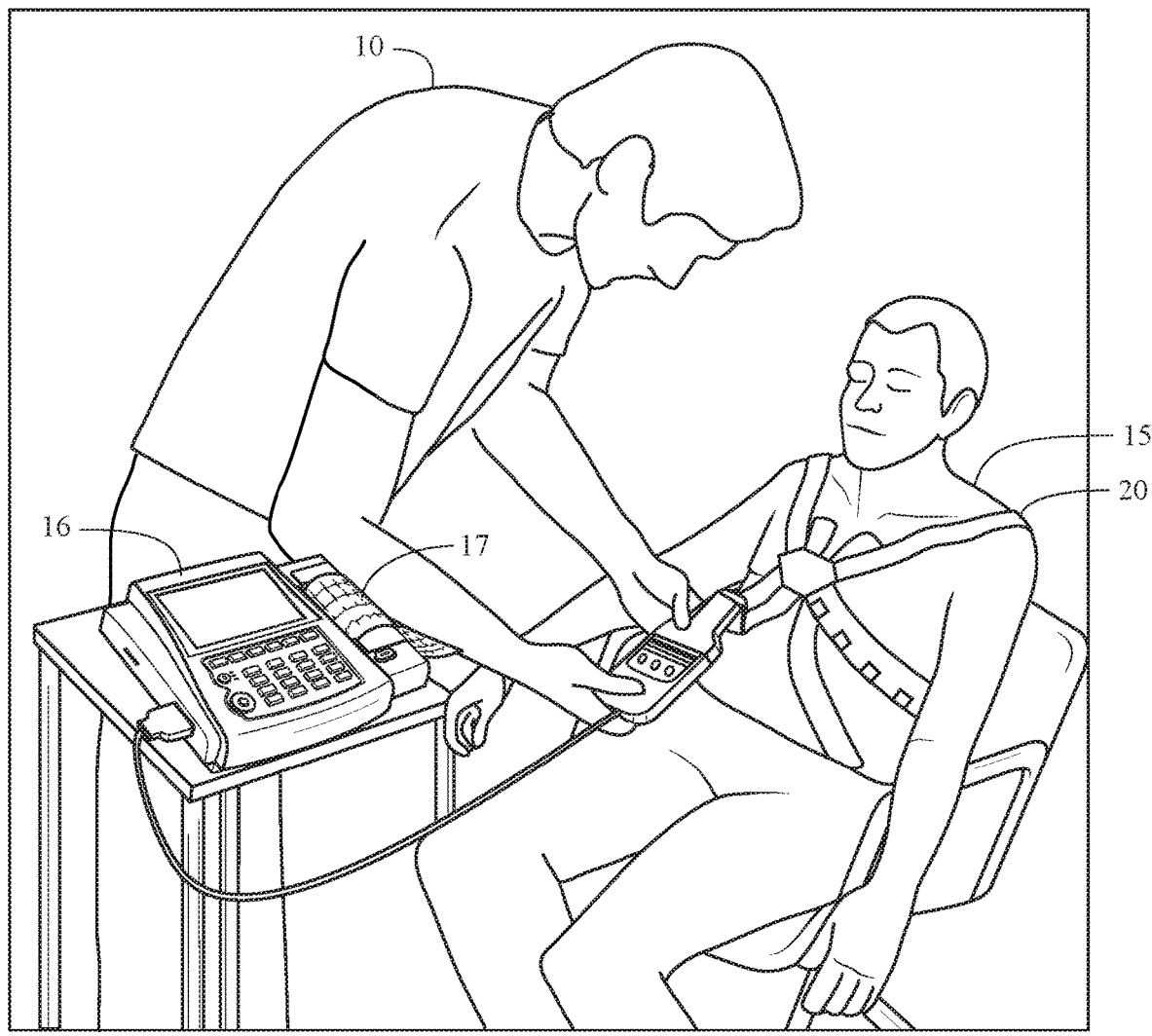
FIG. 1 is an illustration of an emergency cardiac and ECG electrode placement system used by a technician on a patient.

As shown in FIG. 1, the emergency cardiac and electrocardiogram (ECG) electrode placement device ("EXG device") 20 is a worn device that incorporates electrical conducting materials and elastic material into a pad that is applied to the chest wall placing the electrodes in the appropriate anatomic locations on a patient 15. A technician 10, such as an emergency responder, places the EXG device 20 on the patient 15 and connects the EXG device 20 to an ECG machine 16 which generates an ECG 17.

Figure 3:
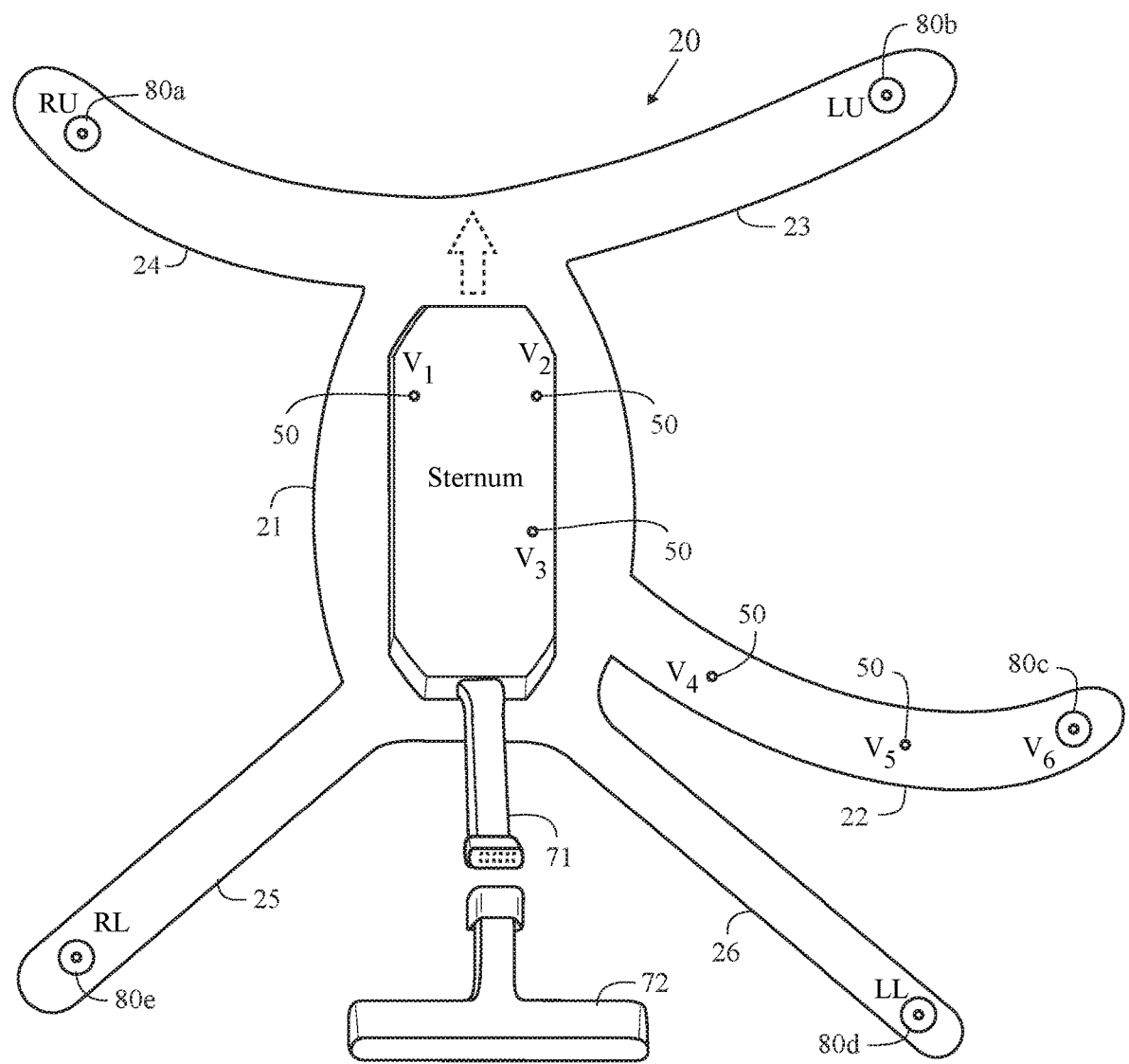
FIG. 3 is top plan view of a first embodiment of an emergency cardiac and ECG electrode placement device in an application state.

As shown in FIG. 3, the EXG device 20 preferably comprises a body 21, electrodes 50, cables 60 (not shown), and an electrode connector 71. The body 21 preferably comprises a first extension member 22, a second extension member 23, a third extension member 24, a fourth extension member 25 and a fifth extension member 26. The electrode connector 71 is positioned on the body 21. Each extension member 22-26 preferably has a width ranging from 1 cm to 10 cm, and a length ranging from 5 cm to 20 cm.

Figure 5:
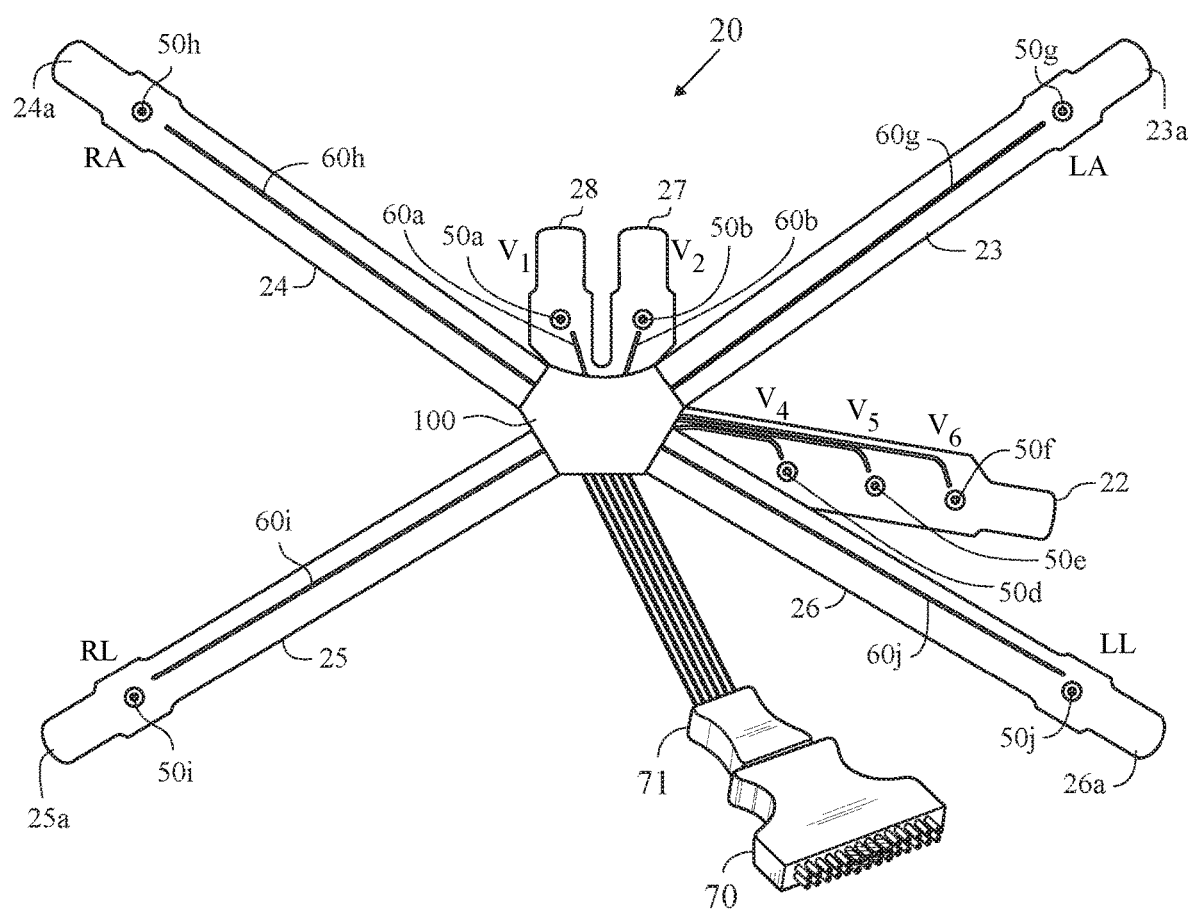
FIG. 5 is a top plan view of a second embodiment of an emergency cardiac and ECG electrode placement device in an application state.
Figure 6:
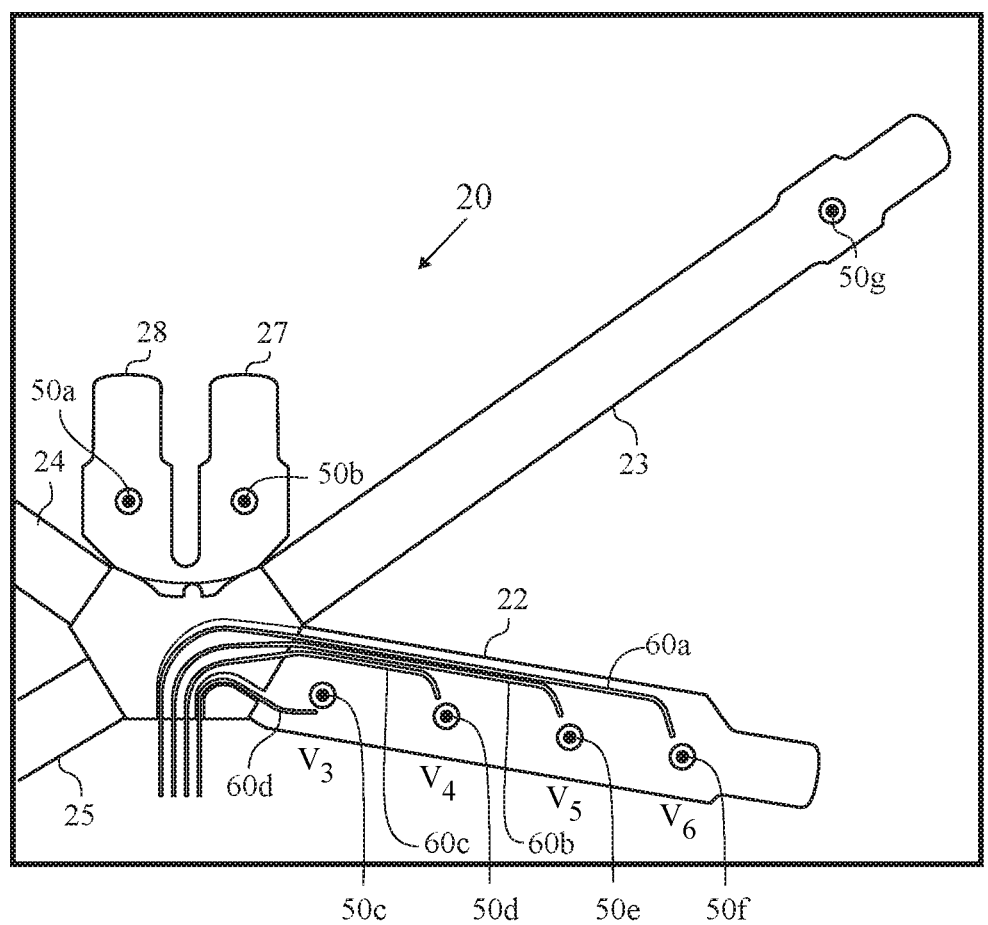
FIG. 6 is an isolated top plan view of a second embodiment of an emergency cardiac and ECG electrode placement device in an application state.
Figure 7:
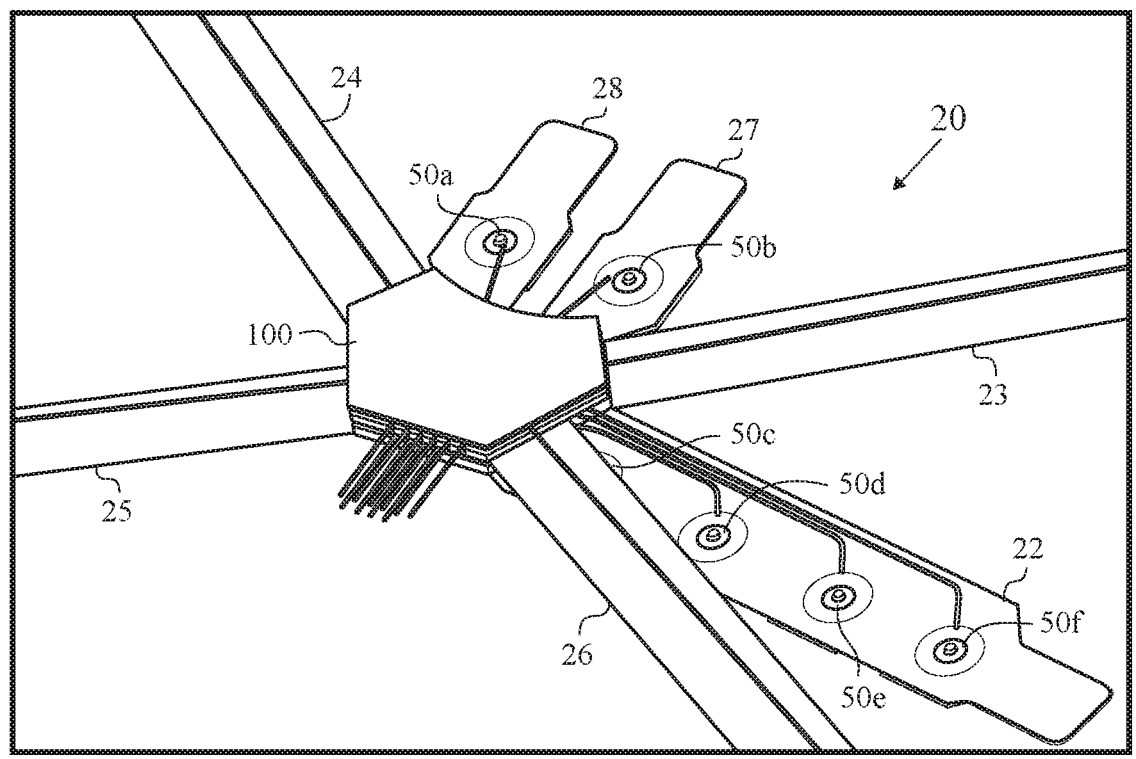
FIG. 7 is a top perspective view of a second embodiment of an emergency cardiac and ECG electrode placement device in an application state.
Figure 8:
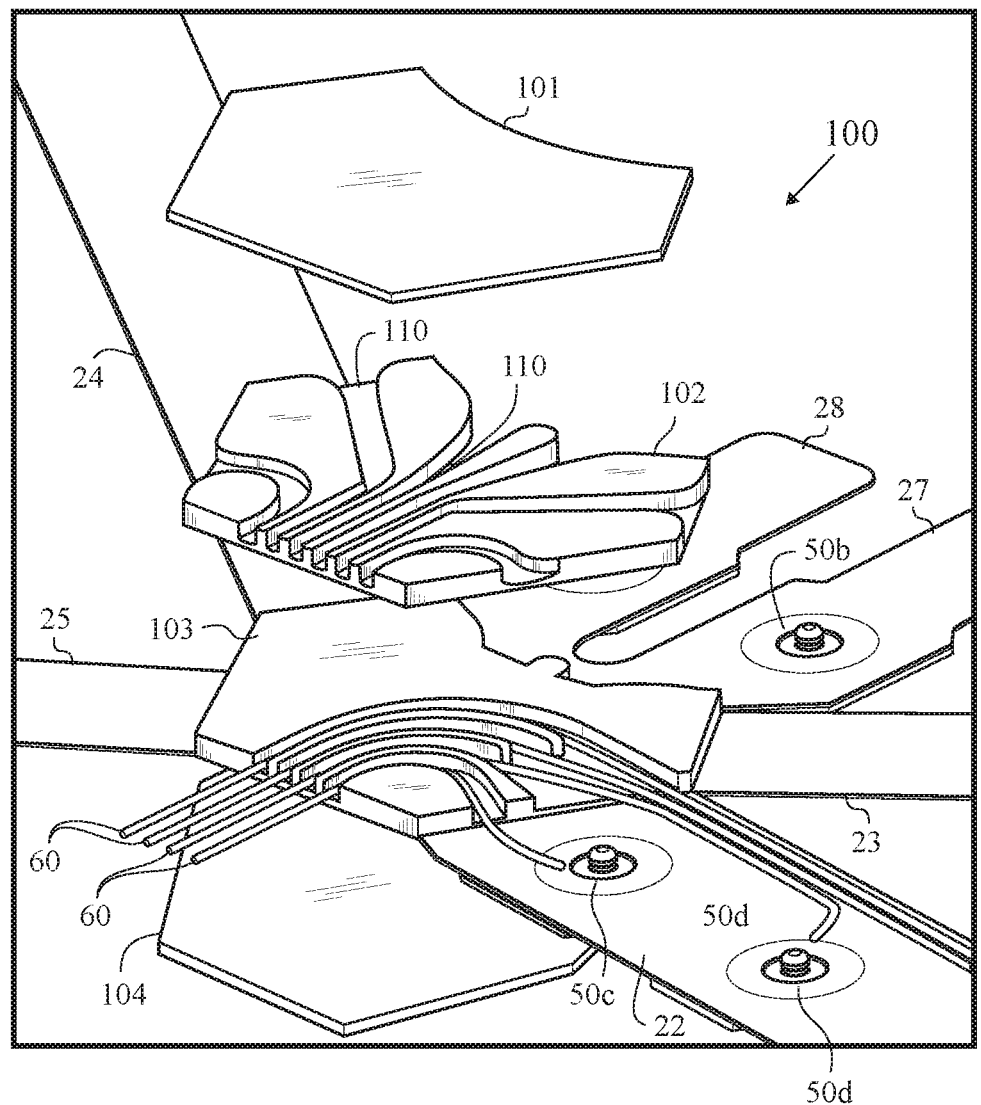
FIG. 8 is an isolated exploded view of a control module of a second embodiment of an emergency cardiac and ECG electrode placement device.

A second embodiment of EXG device 20 is shown in FIGS. 5-7. Each of the first extension member 22, the second extension member 23, the third extension member 24, the fourth extension member 25, the fifth extension member 26, the sixth extension member 27, and the seventh extension member 28 extends outward from a cable management module 100. The seventh extension member 28 comprises a first electrode 50*a*, the sixth extension member comprises a second electrode 50*b*, the first extension member 22 comprises a third electrode 50*c*, a fourth electrode 50*d*, a fifth electrode 50*e* and a sixth electrode 50*f*. A cable 60*a* connects the electrode 50*a* to the electrode connector 71. A cable 60*b* connects the electrode 50*b* to the electrode connector 71. A cable 60*c* connects the electrode 50*c* to the electrode connector 71. A cable 60*d* connects the electrode 50*d* to the electrode connector 71. A cable 60e connects the electrode 50e to the electrode connector 71, and a cable 60f connects the electrode 50f to the electrode connector 71.

A seventh electrode 50g is positioned at a far end 23a of the second extension member 23, and a cable 60g connects the electrode 50g to the electrode connector 71. An eighth electrode 50h is positioned at a far end 24a of the third extension member 24, and a cable 60h connects the electrode 50h to the electrode connector 71. A ninth electrode 50i is positioned at a far end 25a of the fourth extension member 25, and a cable 60i connects the electrode 50i to the electrode connector 71. A tenth electrode 50j is positioned at a far end 26a of the fifth extension member 26, and a cable 60j connects the electrode 50j to the electrode connector 71. The far ends 23a, 24a, 25a, 26a of the extension members 23, 24, 25, 26 and even the far end of extension member 22, act as strip extensions that assist in placing the electrode correctly. This strip extension is approximately 1 to 2 inches in length as measured from the electrode.

The EXG device 20 of FIG. 5 has to the electrode connector 71 connected to a connector module 70.

The EXG device 20 of FIGS. 5-8 includes a cable management module 100. The cable management module 100 comprises an upper cover 101, an upper guide piece 102, a lower guide piece 103 and a lower cover 104. Each of the upper guide piece 102 and the lower guide piece 103 has a plurality of channels 110 therein for guiding the cables 60 therethrough. The channels 110 of the cable management module 100 allow for the extension of an extension member to fit a patient, without the cables 60 becoming tangled.

Figure 9:
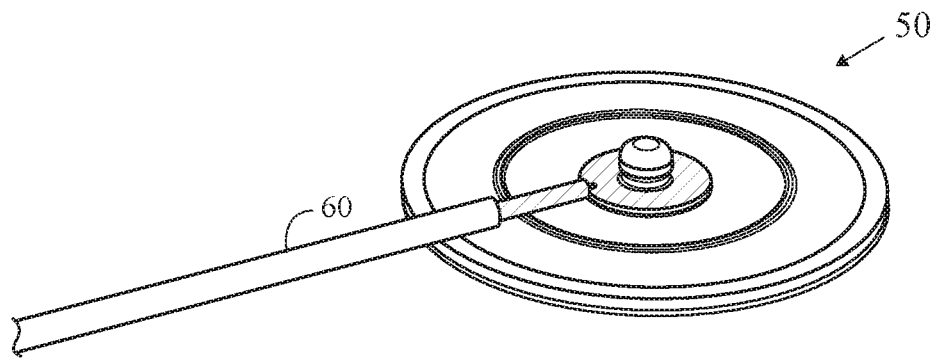
FIG. 9 is an isolated top perspective view of an electrode of an emergency cardiac and ECG electrode placement device.
Figure 10:
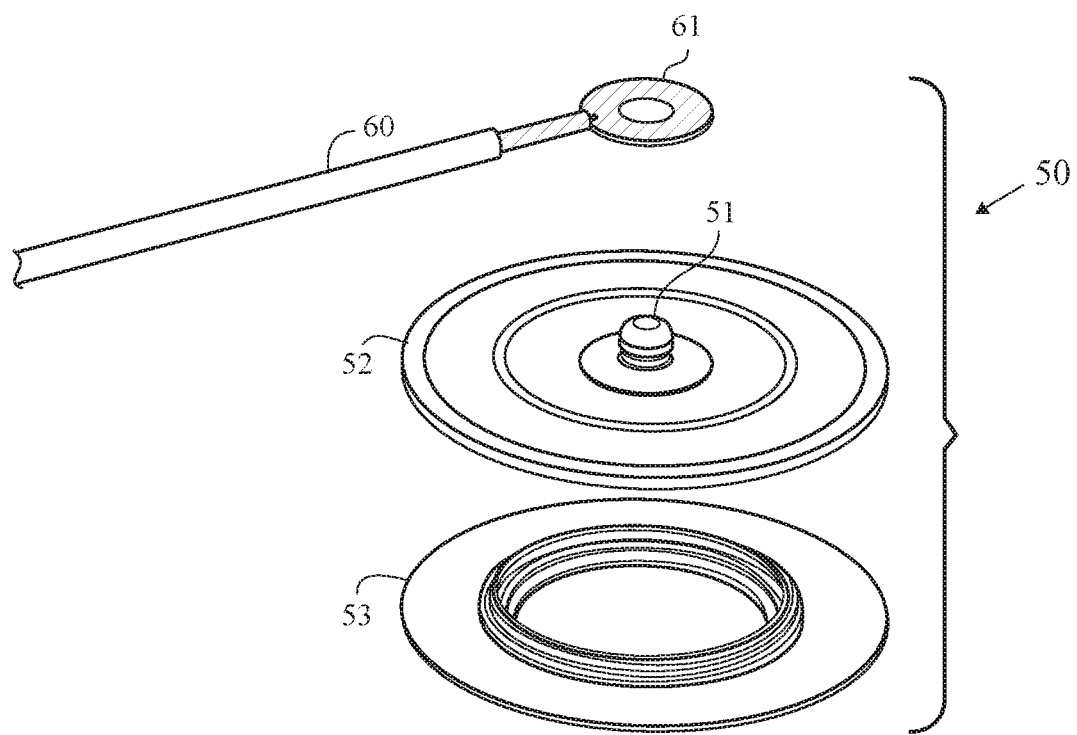
FIG. 10 is an isolated exploded view of an electrode of an emergency cardiac and ECG electrode placement device.
Figure 11:
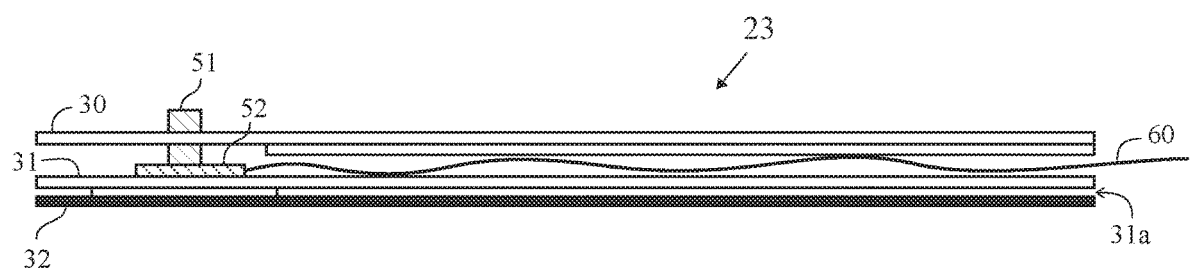
FIG. 11 is an isolated cross-sectional view of an extension of is an isolated view of an electrode of an emergency cardiac and ECG electrode placement device.

As shown in FIG. 11, each extension member of the body 21 preferably comprises a base layer 30 composed of a flexible material, an adhesive layer 31 composed of a flexible material, and a backing layer 32 attached to an adhesive surface 31a of the adhesive layer 31. One preferred material for the flexible material is KT TAPE from Spidertech. The base layer 30 preferably has a Shore A hardness ranging from 50 to 90, which better allows for chest compressions. One preferred material for the adhesive layer is an adhesive from 3M. As shown in FIGS. 9-10, each of the electrodes 50 preferably comprises a connection stud 51, a contact pad interface 52 and a contact pad 53. Each contact pad 53 is preferably has a diameter ranging from 30 millimeters ("mm") to 40 mm, and most preferably 35 mm, to allow for retention of a gel protector. Each contact pad 53 is preferably composed of a material from 3M. A cable connector 61 of each cable 60 is connected to a connection stud 51 of each electrode 50 preferably using a conductive epoxy. Each cable connector 61 is preferably composed of 0.2 mm thick copper, with a 26 mm inside diameter. Each cable 60 of the plurality of cables 60 is positioned between the base layer 30 and the adhesive layer 31. Each cable 60 is connected to a corresponding electrode 50 of the plurality of electrodes 50 and connected to the electrode connector 71. Each cable 60 is preferably shielded to prevent electrical interference.

Each of the plurality of cables preferably as an outer diameter ranging from 0.008 inch to 0.310 inch.

Figure 2:
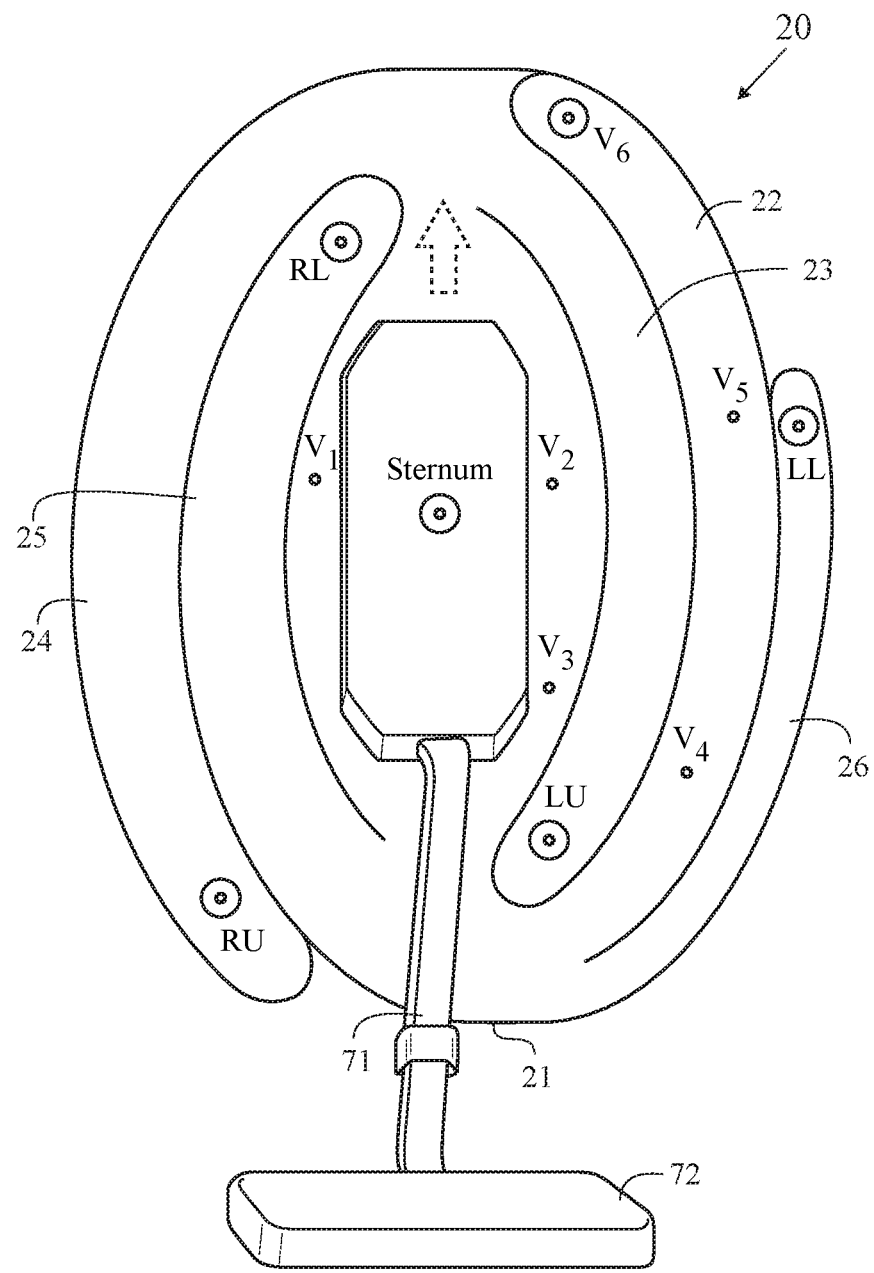
FIG. 2 is a top plan view of a first embodiment of an emergency cardiac and ECG electrode placement device in a storage state.
Figure 4:
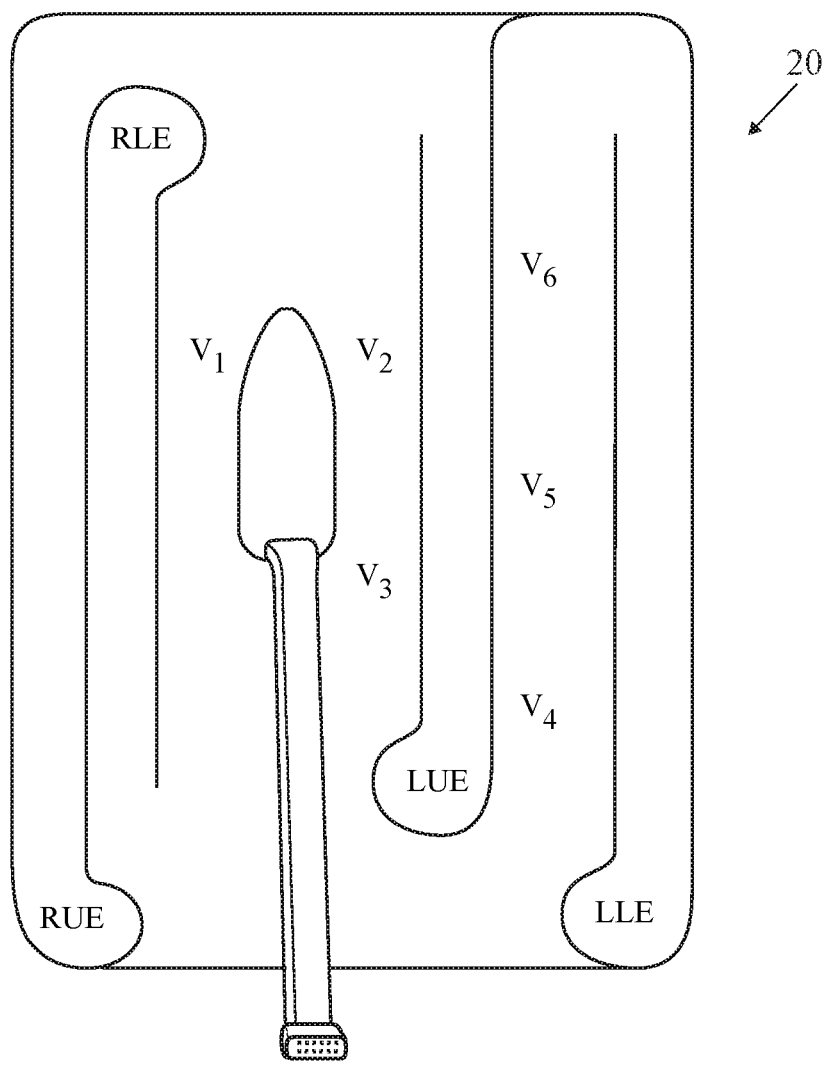
FIG. 4 is a side elevation view of a first embodiment of an emergency cardiac and ECG electrode placement device in a storage state.

As shown in FIGS. 2 and 4, the EXG device 20 is preferably provided in a compact, easily stored and transported form, that is then applied to a patient's chest wall with materials that have adhesive capabilities that preferably resist moisture and conforms to the patient's body with inherent elasticity with placement of electrodes within a pad that maintain proper anatomic ratios and locations. The EXG device 20 preferably remains adherent to the patient's body through the duration of the acute pre-hospital and transition through the emergency department and acute hospitalization care periods (which is typically three days), but the EXG device 20 remains easily removable, while tolerating physiologic changes such as sweat, fever and medical treatment such as cardiac pulmonary resuscitation ("CPR"). The EXG device 20 is clearly marked and designed to fit to the chest wall so that its application ensures proper placement of all electrodes on the patient. The incorporated electrical conducting materials come together into a single cable/wire that is either directly or indirectly joined to an ECG monitoring device. The cable has adaptor capability that allows for wireless transfer of data to an ECG monitoring device obviating the need for having a bulky ECG machine in close proximity to the patient. The single cable also eliminates the need for multiple wires on a patient. Multiple wires that could potentially interfere with diagnostic imaging such as chest radiographs, or interfere with placement of emergency medical equipment such as transcutaneous cardiac pacer pads or defibrillating pad.

The EXG device 20 reduces the time to perform ECG testing significantly. With proper training, a user can anticipate ECG acquisition in less than one minute, and potentially within seconds. Current ECG data can take several minutes or longer depending on the care setting. It is not unusual for an ECG ordered in a hospital setting to take more than 10-30 minutes.

The EXG device 20 also eliminates lead transposition error. That is, the attachment of an electrode wire in a wrong electrode.

The EXG device 20 makes ECG data more reliable and reproducible. There is no variation in lead placement while performing serial ECGs—which is often done in the hospital and pre-hospital setting. The incorporated elastic electroconductive materials allow for this small form factor to accommodate varying body types (man, women, adult, child, obese, anorexic) while maintaining strict anatomic ratios and correct placement and ensure proper lead placement.

The ease of use of the EXG device 20 makes ECG acquisition less inconvenient and potentially improves ECG utilization in the pre-hospital setting.

The EXG device 20 also reduces the frequency of lead detachment.

An alternative embedment of the EXG system has wireless transfer capability that makes acquisition of the ECG in any situation feasible.

The EXG device 20 preferably incorporates either integrated elastic electro-conductive materials or printable elastic electro-conductive material used in the acquisition of electrical signals from the electrodes.

The EXG device 20 adheres to skin surfaces through a variety of physiologic conditions not currently met by current methods.

The EXG system allows for acquisition of data in settings that standard methods currently fail.

Existing technology for ECG acquisition relies on technical expertise in lead placement.

Removing technical error is dependent of operator knowledge and skill, as well as interpretation of ECG data to identify systemic error in placement.

The time to acquire an ECG is dependent on many factors but is limited due to the number of electrodes that are placed on the chest and torso, which then need to be attached to the ECG device. There are preferably a minimum of ten wires involved, and more electrodes are possible to allow for more specific views of the right side of the heart and/or posterior heart leads.

The EXG device 20 is preferably a single device with embedded lead placement through a wearable material (such as a fabric) with a small physical footprint with the elasticity to maintain physiologic measurement across different ages, gender and body habitus without requiring multiple sized devices.

In one embodiment, the EXG device preferably comprises: adhesive stretchable material that is breathable and water/sweat resistant; embedded elastic electroconductive material conducting electrical signals from the integrated cardiac electrodes to a central data cable; embedded elastic electroconductive material/wiring/cabling arranged to allow for stretching across body types and sizes; electrode connection port; Bluetooth capable emitter and receiver; conduction gel; and embedded electrodes (manufactured or printable).

The elastic adhesive membrane preferably provides adherence to body surface. It is preferably tolerant to moisture. The EXG device preferably incorporates electroconductive materials and electrodes that conduct signal from the skin to a single data cable/wire. The EXG device preferably expands in an elastic fashion to appropriately fit varied body types while meeting exact ratios of electrode distance without distortion. The EXG device preferably has significant stability of size and shape with elastic components to make it easily applicable to the chest wall. The EXG device preferably comes in a compact form factor.

In one embodiment, there is encapsulated expandable electroconductive material within the membrane. Within the elastic membrane is incorporated electroconductive materials that originate from each electrode to come together into a single data cable encompassing a minimum of ten ECG wires to allow for a standard twelve lead ECG (by convention there are two leads that are inferred from the ten connections).

Alternatively, the EXG device allows for the use of external electrodes. In the event that ECG monitoring equipment is not compatible with the data cable, electrodes at the ascribed anatomical locations can be accessed with standard medical cardiac monitoring and ECG devices.

In one embodiment, there is a conductive membrane at ECG electrode sites. At the ascribed electrode ECG locations is a typical electroconductive Ag/AgCL membrane to conduct current from body surface to ECG monitoring device.

In one embodiment, a data cable brings individual electrodes into one cable that encompasses a minimum of ten wires/leads of the typical ECG analysis which is then compatible with various ECG devices and wireless transfer system. Other conductive interfaces may be utilized with the invention including ones composed of graphene/carbon, nickel, and copper.

In use, one applies the EXG device 20 to an anterior chest wall overlying the sternum symmetrically at a level above the nipple line of the patient and below the sternal notch, removing the backing layer 32 to expose the adhesive surface 31*a* of the adhesive layer 31. The precordial limb is then stretched to the lateral chest wall at the mid axillary line below the nipple line. Similarly each limb will have the backing layer 32 removed in succession to expose the adhesive surface 31*a* of the adhesive layer 31. The right upper extremity limb is stretched towards the right shoulder. The left upper extremity is stretched towards the left shoulder. The right lower extremity limb is stretched to the right lower abdominal quadrant. The left lower extremity limb is stretched to the left lower abdominal quadrant. The cable is either attached to directly to the ECG device cable. Or in versions utilizing a BLUETOOTH transceiver, then the EXG device 20 is activated to sync with the BLUETOOTH transceiver that is already connected to the ECG device.

Figure 12:
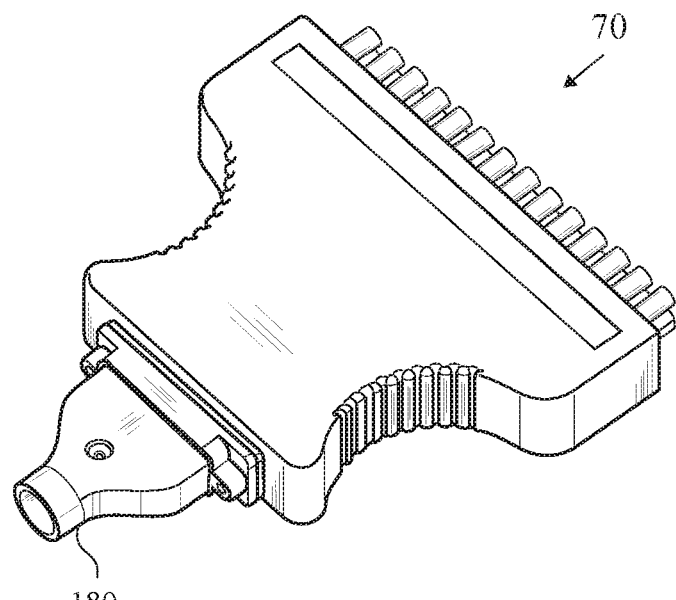
FIG. 12 is a top perspective view of a connection module for an emergency cardiac and ECG electrode placement device.
Figure 13:
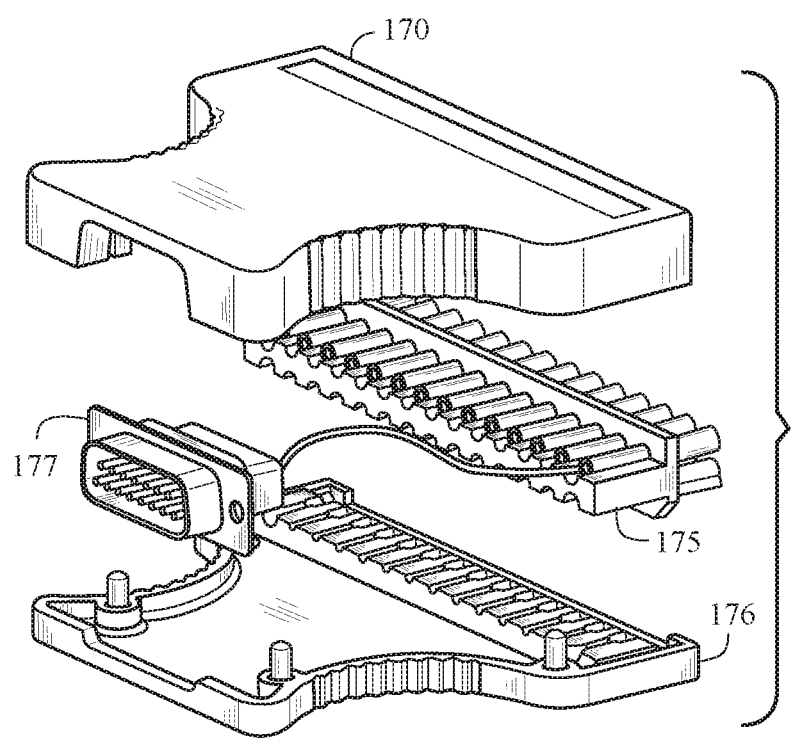
FIG. 13 is an exploded top perspective view of a connection module for an emergency cardiac and ECG electrode placement device.

A preferred embodiment of a connector module 70 is shown in FIGS. 12-13. The connector module 70 preferably comprises a top cover portion 170, a bottom cover portion 176, a plurality of connector pins 175 and a fifteen pin sub connector 177. An interface connector 180 is also shown.

Figure 14:
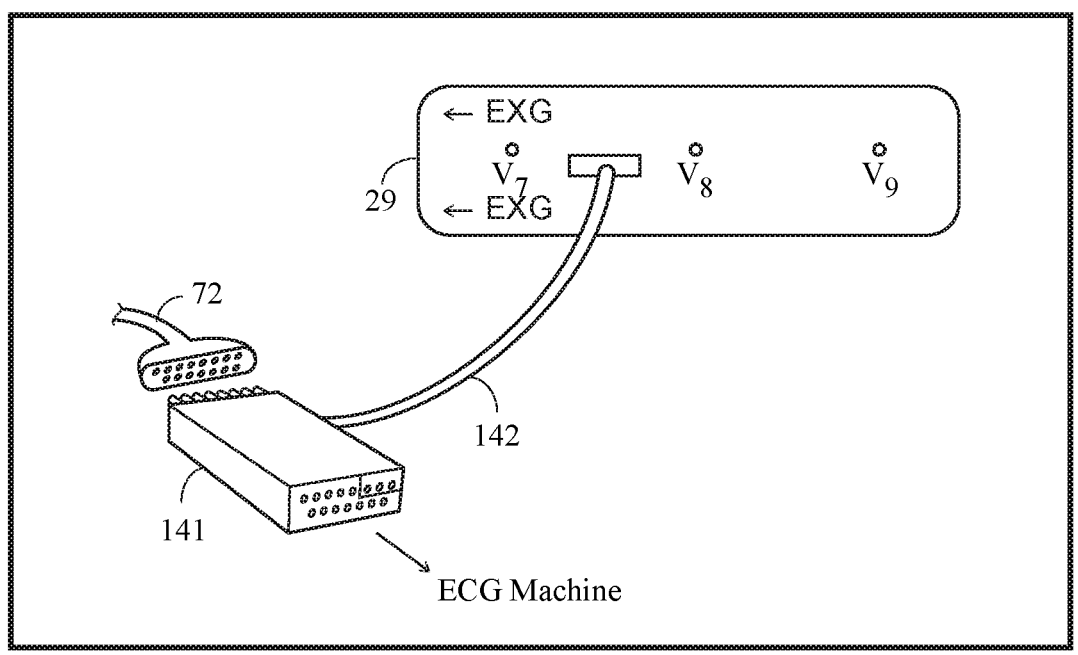
FIG. 14 is an isolated view of a side extension for an emergency cardiac and ECG electrode placement device.

A posterior extension member 29 is shown in FIG. 14. This additional posterior extension member 29 preferably has multiple electrodes that connect via cable 142 to an intermediary adapter module 141 which connects to the electrode connector 72. The posterior leads preferably are connected through the adapter module 141 onto the end of the original EXG device 20 and basically take over leads V5-6 for the standard ECG.

Figure 15A:
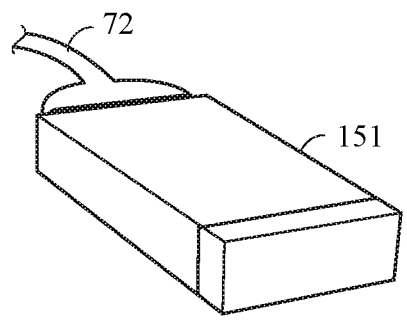
FIG. 15A is an isolated view of a wireless emitter for an emergency cardiac and ECG electrode placement system.
Figure 15B:
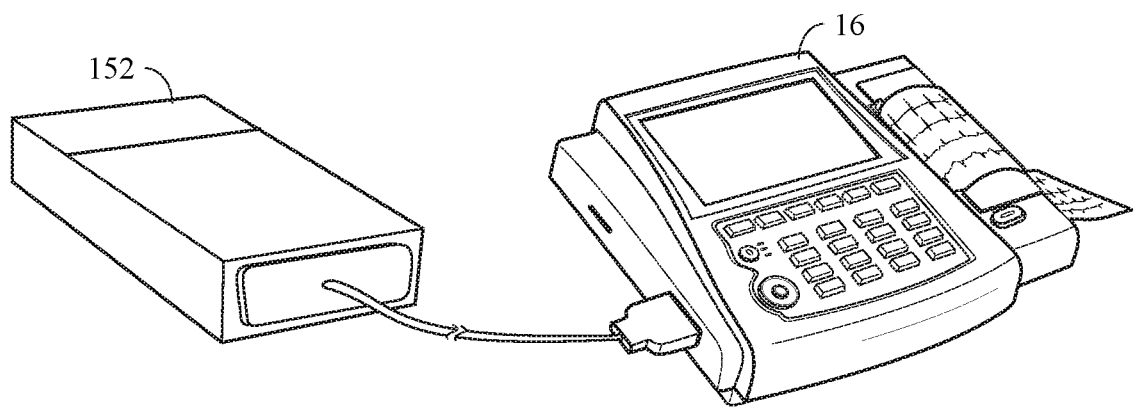
FIG. 15B is an isolated view of a wireless receiver for an emergency cardiac and ECG electrode placement system.

As shown in FIGS. 15A and 15B, in an alternative embodiment, the EXG device 20 comprises a wireless emitter 151 and a wireless receiver 152. The wireless emitter 151 is connected to electrode connector 72, and the wireless receiver is connected to the ECG machine 16. The wireless emitter 151 and the wireless receiver 152 preferably operation on a BLUETOOTH communication protocol. However, those skilled in the pertinent art will recognize that other wireless communication protocols may be utilized with the alternative embodiment of the EXG device 20 without departing from the scope and spirit of the present invention.

Figure 16:
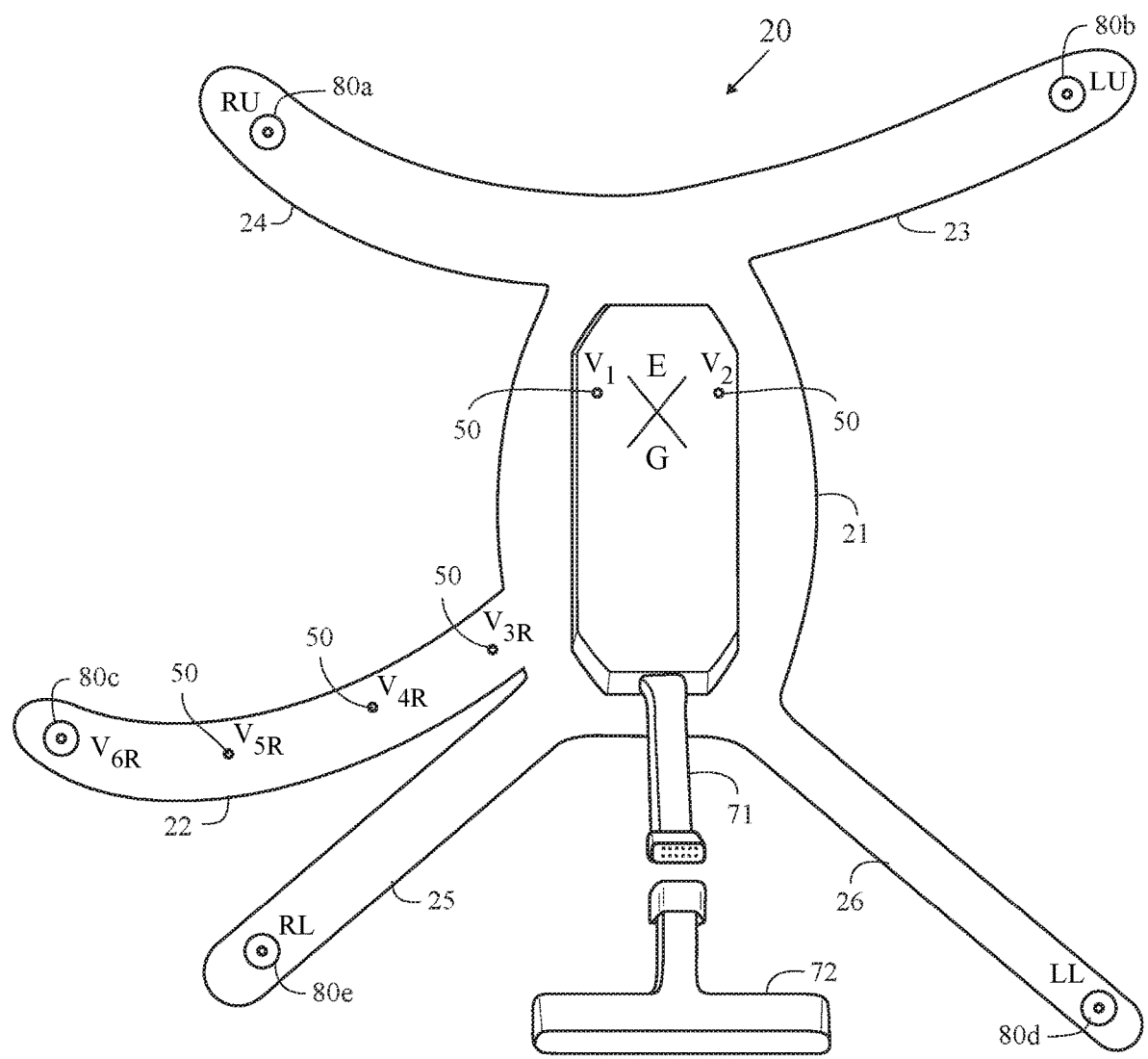
FIG. 16 is a bottom plan view of a second embodiment of an emergency.

As shown in FIG. 16, the EXG device 20 also preferably comprises a plurality of external electrodes 80. A third extension member 24 comprises a first external electrode 80*a*. A second extension member 23 comprises a second external electrode 80*b*. A first extension member 22 comprises a third external electrode 80*c*. A fifth extension member 26 comprises a fourth external electrode 80*d*. A fourth extension member 25 comprises a fifth external electrode 80*e*.

Figure 17:
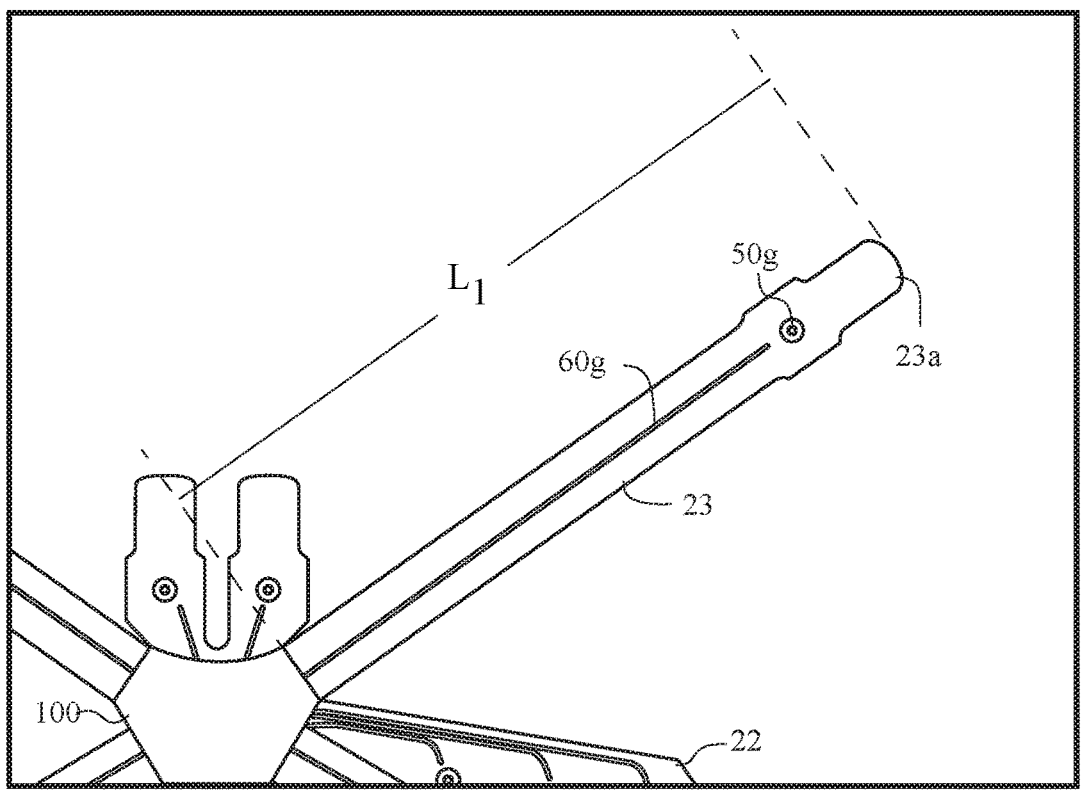
FIG. 17 is an isolated top plan view of a second embodiment of an emergency cardiac and ECG electrode placement device in an application state with an un-extended extension.
Figure 17A:
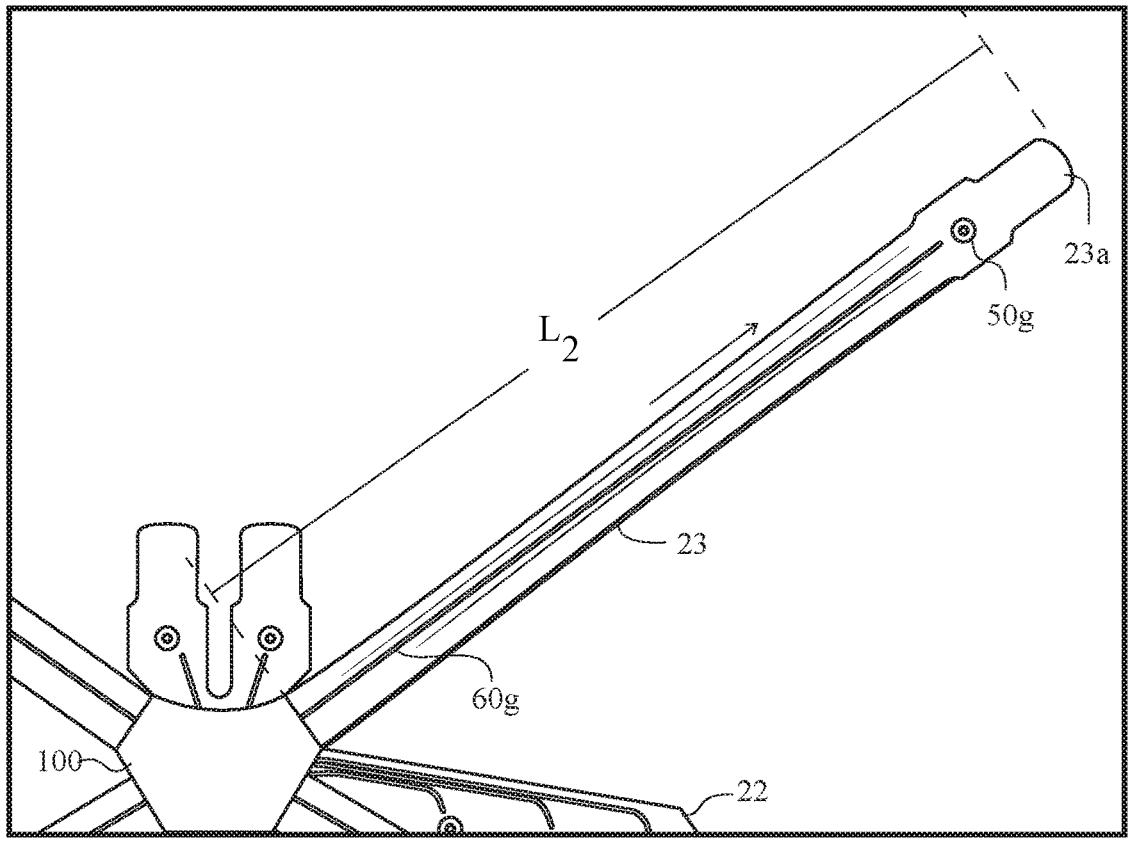
FIG. 17A is an isolated top plan view of a second embodiment of an emergency cardiac and ECG electrode placement device in an application state with an extended extension.

FIGS. 17 and 17A illustrate the stretching capability of the extension members of the EXG device 20. The extension member 23 extends from a length L1 (as shown in FIG. 17) to a length L2 (as shown in FIG. 17A). In a preferred embodiment, each extension member 23, 24, 25 and 26 extends from a length L1 ranging from 7.0 to 14.0 inches to a length L2 ranging from 10.0 to 16.5 inches. In a most preferred embodiment, L1 ranges from 10 to 11 inches, and L2 ranges from 12 to 13 inches. A width of each extension member 22, 23, 24, 25, 26 preferably ranges from 1 centimeter ("cm") to 10 cm, and most preferably 2.5 cm to 5 cm. A thickness of each extension member 22, 23, 24, 25, 26 preferably ranges from 0.1 inch to 0.5 inch.

Figure 18:
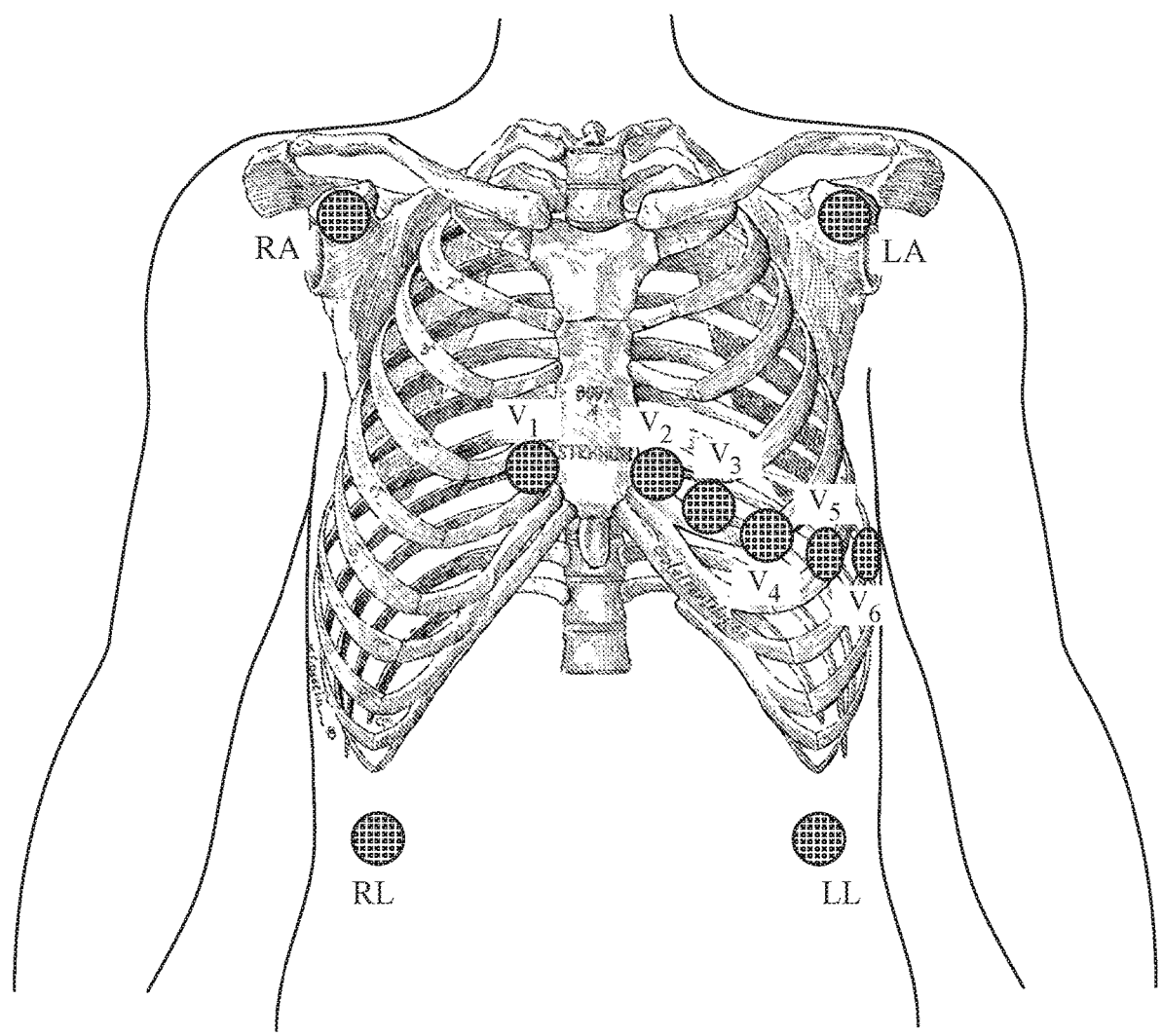
FIG. 18 is an illustration of a human body showing a chest skeleton and markers for electrode placement.

FIG. 18 is an illustration of a human body showing a chest skeleton and markers for electrode placement.

Figure 19:
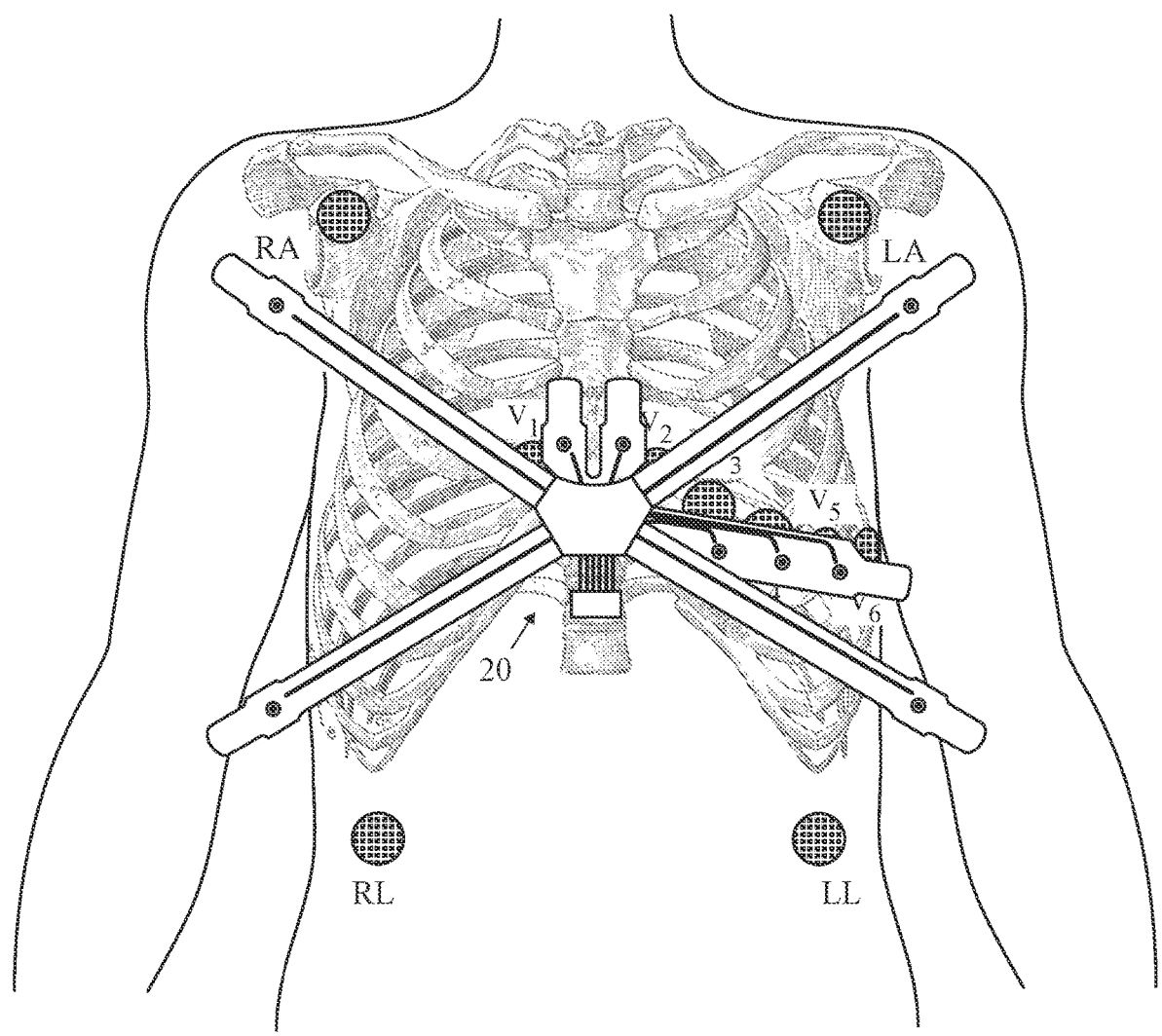
FIG. 19 is an illustration of a human body showing a chest skeleton and markers for electrode placement with an overlay of the emergency cardiac and ECG electrode placement device.

FIG. 19 is an illustration of a human body showing a chest skeleton and markers for electrode placement with an overlay of the emergency cardiac and ECG electrode placement device 20.

The emergency cardiac and ECG electrode placement device 20 is capable of being applied to a patient while an emergency vehicle is in motion since the device 20 is applied to and adheres to a patient's chest area, which mitigates signal loss. Likewise, the emergency cardiac and ECG electrode placement device 20 is capable of being applied to a patient that is moving due to a seizure, aggressiveness, and the like.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. An emergency cardiac and electrocardiogram (ECG) electrode placement device, the device comprising:
   a body comprising a plurality of extension members, wherein the body comprises a base layer composed of a flexible material, an adhesive layer composed of a flexible material, and a backing layer attached to an adhesive surface of the adhesive layer;
   a plurality of electrodes, each of the plurality of electrodes comprising a connection stud, a contact pad interface and a contact pad;
   a plurality of cables; and
   an electrode connector connected to each of the plurality of cables;
   wherein each cable of the plurality of cables is positioned between the base layer and the adhesive layer, and connected to a corresponding electrode of the plurality of electrodes;
   wherein a sixth extension member of the plurality of extension members comprises a first electrode of the plurality of electrodes;
   wherein a seventh extension member of the plurality of extension members comprises a second electrode of the plurality of electrodes;
   wherein a first extension member of the plurality of extension members comprises a third electrode, a fourth electrode, a fifth electrode and a sixth electrode of the plurality of electrodes;
   wherein a seventh electrode of the plurality of electrodes is positioned at a far end of a second extension member of the plurality of extension members;
   wherein an eighth electrode of the plurality of electrodes is positioned at a far end of a third extension member of the plurality of extension members;
   wherein a ninth electrode of the plurality of electrodes is positioned at a far end of a fourth extension member of the plurality of extension members;
   wherein a tenth electrode of the plurality of electrodes is positioned at a far end of a fifth extension member of the plurality of extension members.

2. The device according to claim 1 wherein each extension member has a width ranging from 1 cm to 10 cm, and a length ranging from 5 cm to 20 cm.

3. The device according to claim 1 further comprising a cable management module attached to the body.

4. An emergency cardiac and electrocardiogram (ECG) electrode placement device, the device comprising:
   a cable management module comprising an upper cover, an upper guide piece, a lower guide piece and a lower cover wherein each of the upper guide piece and the lower guide piece has a plurality of channels therein;
   a body connected to the cable management module, the body comprising a plurality of extension members wherein the body comprises a base layer composed of a flexible material, an adhesive layer composed of a flexible material, and a backing layer attached to an adhesive surface of the adhesive layer;
   a plurality of electrodes positioned on the body, each of the plurality of electrodes comprising a connection stud, a contact pad interface and a contact pad;
   a plurality of cables; and
   an electrode connector connected to each of the plurality of cables;
   wherein at least four extension members of the plurality of extension members extend outward from the cable management module;
   wherein each cable of the plurality of cables is positioned between the base layer and the adhesive layer, routed through a channel of the plurality of channels, and connected to a corresponding electrode of the plurality of electrodes.

5. The device according to claim 4 wherein each extension member has a width ranging from 1 cm to 10 cm, and a length ranging from 5 cm to 20 cm.

* * * * *